United States Patent [19]

Guigan

[11] Patent Number: 4,812,411
[45] Date of Patent: Mar. 14, 1989

[54] METHOD OF PERFORMING MEDICAL ANALYSES, AND A CONDITIONING STRIP AND APPARATUS FOR PERFORMING THE METHOD

[76] Inventor: Jean Guigan, 9, rue Jean Mermoz, 75008 Paris, France

[21] Appl. No.: 808,970

[22] Filed: Dec. 16, 1985

[30] Foreign Application Priority Data

Dec. 21, 1984 [FR] France .................................. 84 19719

[51] Int. Cl.$^4$ .................. C12M 1/20; G01N 21/07
[52] U.S. Cl. ..................................... 435/293; 435/301; 422/72; 422/102; 436/45; 356/427; 356/443
[58] Field of Search .............. 435/293, 300, 301, 312, 435/810; 422/72, 102; 436/45

[56] References Cited

U.S. PATENT DOCUMENTS

| | | | |
|---|---|---|---|
| 4,076,592 | 2/1978 | Bradley | 435/301 X |
| 4,077,845 | 3/1978 | Johnson | 435/301 X |
| 4,260,687 | 4/1981 | Jacobson et al. | 435/301 |
| 4,462,964 | 7/1984 | Guigan | 422/102 |
| 4,714,590 | 12/1987 | Guigan | 422/102 |

FOREIGN PATENT DOCUMENTS 73512 3/1983 European Pat. Off. .............. 422/72

Primary Examiner—Samuel Scott
Assistant Examiner—Allen J. Flanigan
Attorney, Agent, or Firm—Sughrue, Mion, Zinn, Macpeak, and Seas

[57] ABSTRACT

The method in accordance with the invention provides antibiograms or bacteriological identification of colonies of micro-organisms. The method uses a cabinet (1) which supports a set of mechanical, thermal, optical, and electronic units, together with conditioning strips in which the various biochemical reactions take place. After being seeded with a micro-organism under investigation, a strip is placed on the cabinet and is then subjected to a sequence of mechanical, thermal, and optical operations.

6 Claims, 17 Drawing Sheets

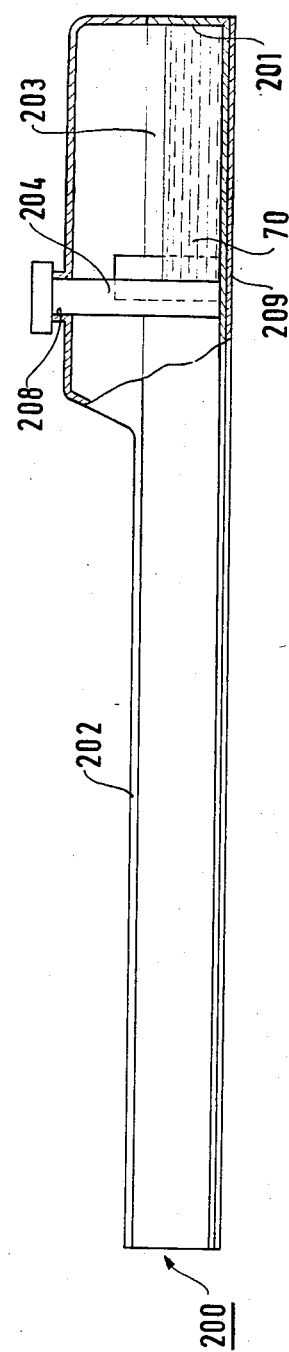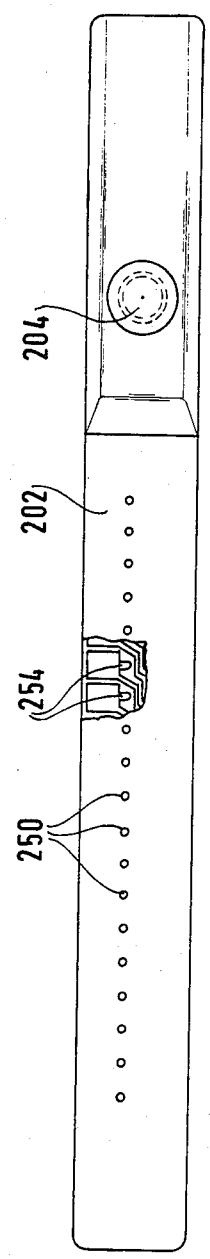

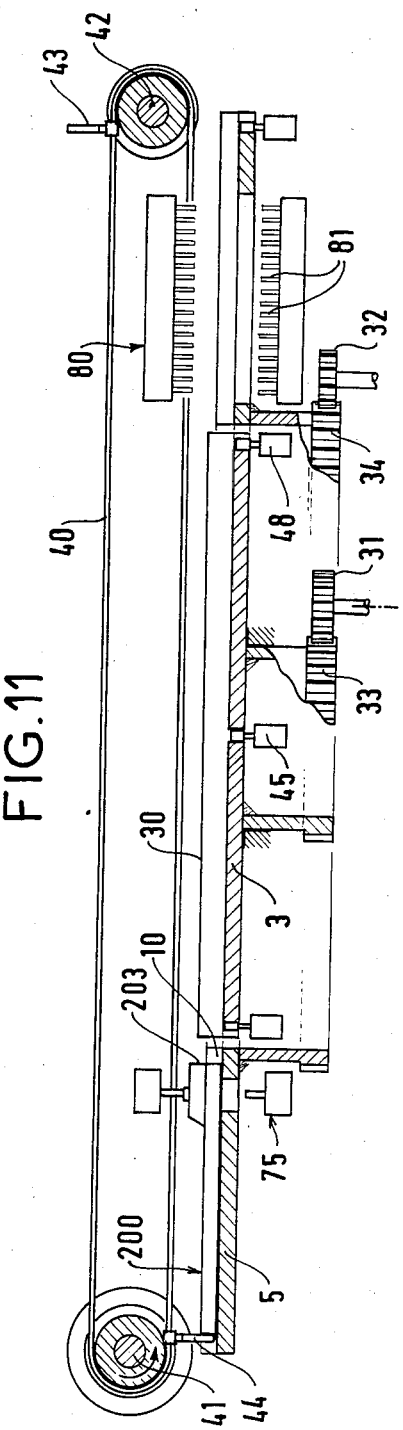
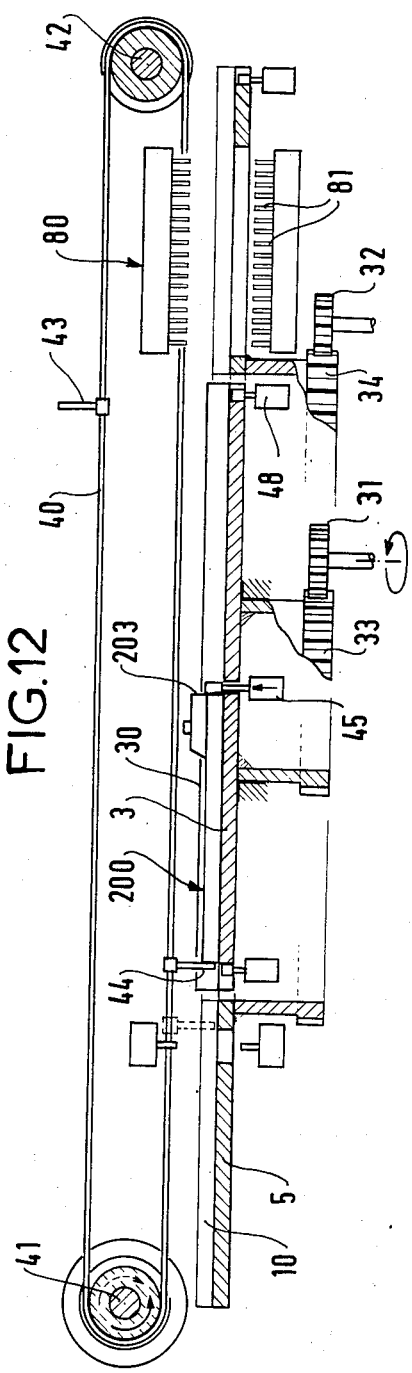
FIG.11
FIG.12

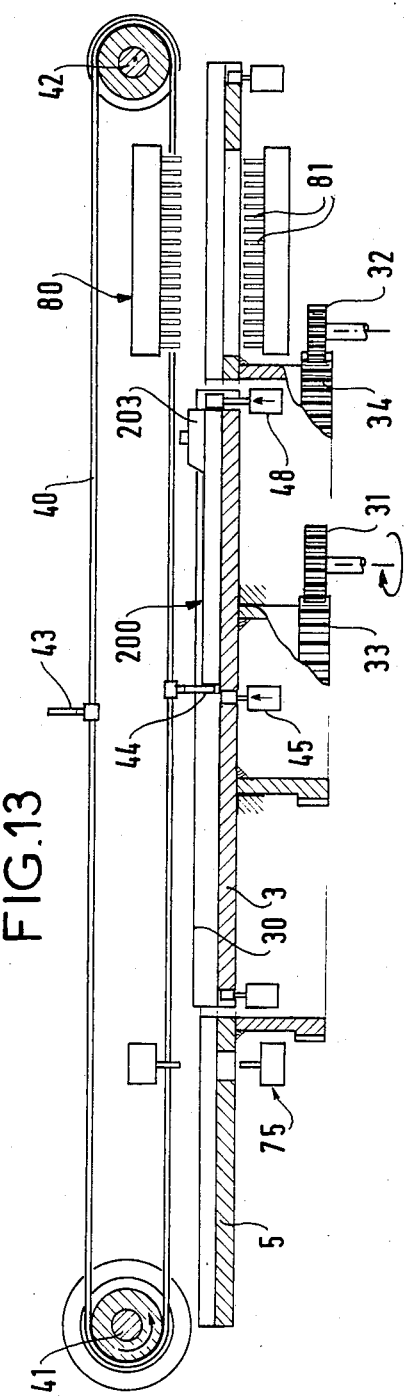
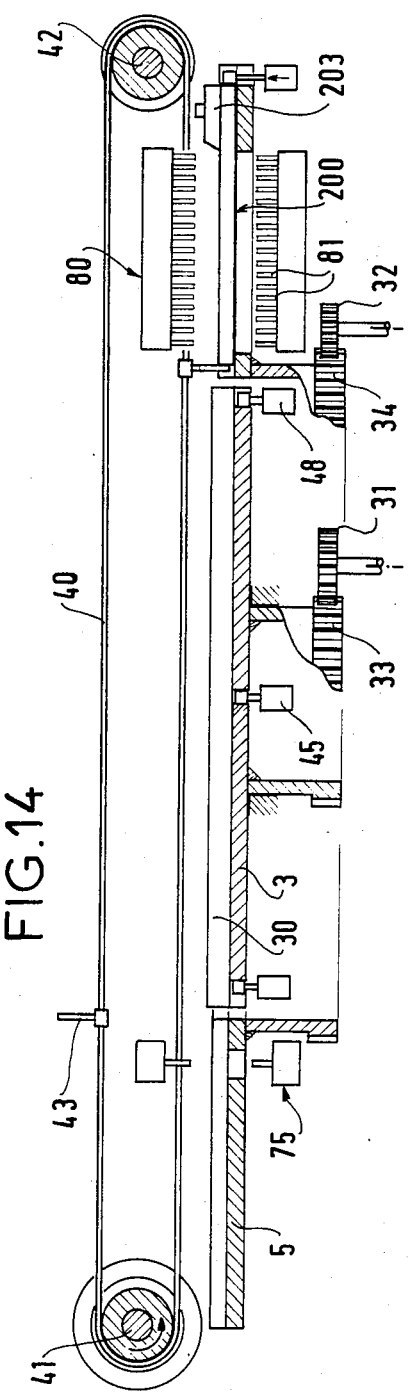
FIG.13
FIG.14

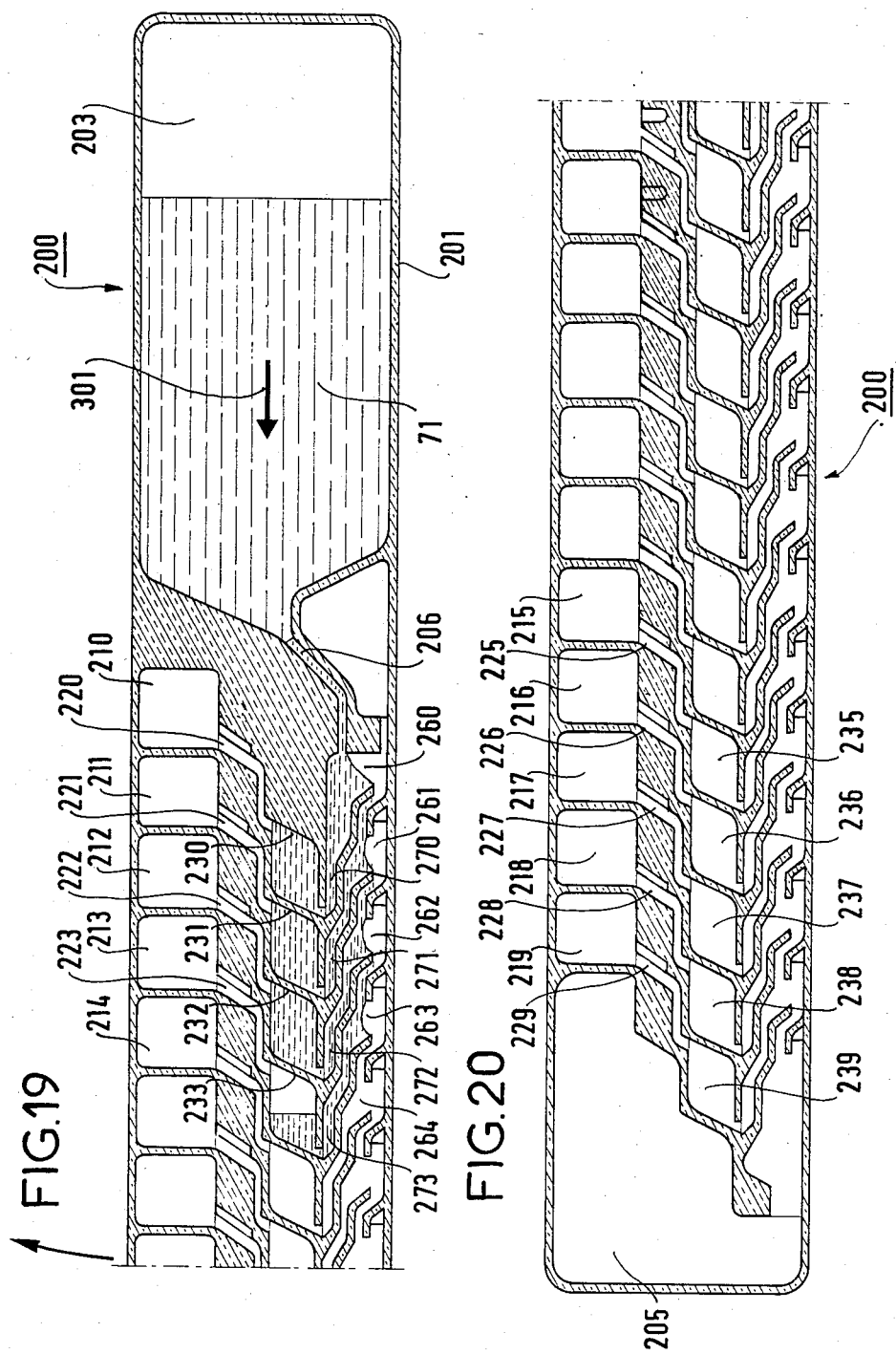

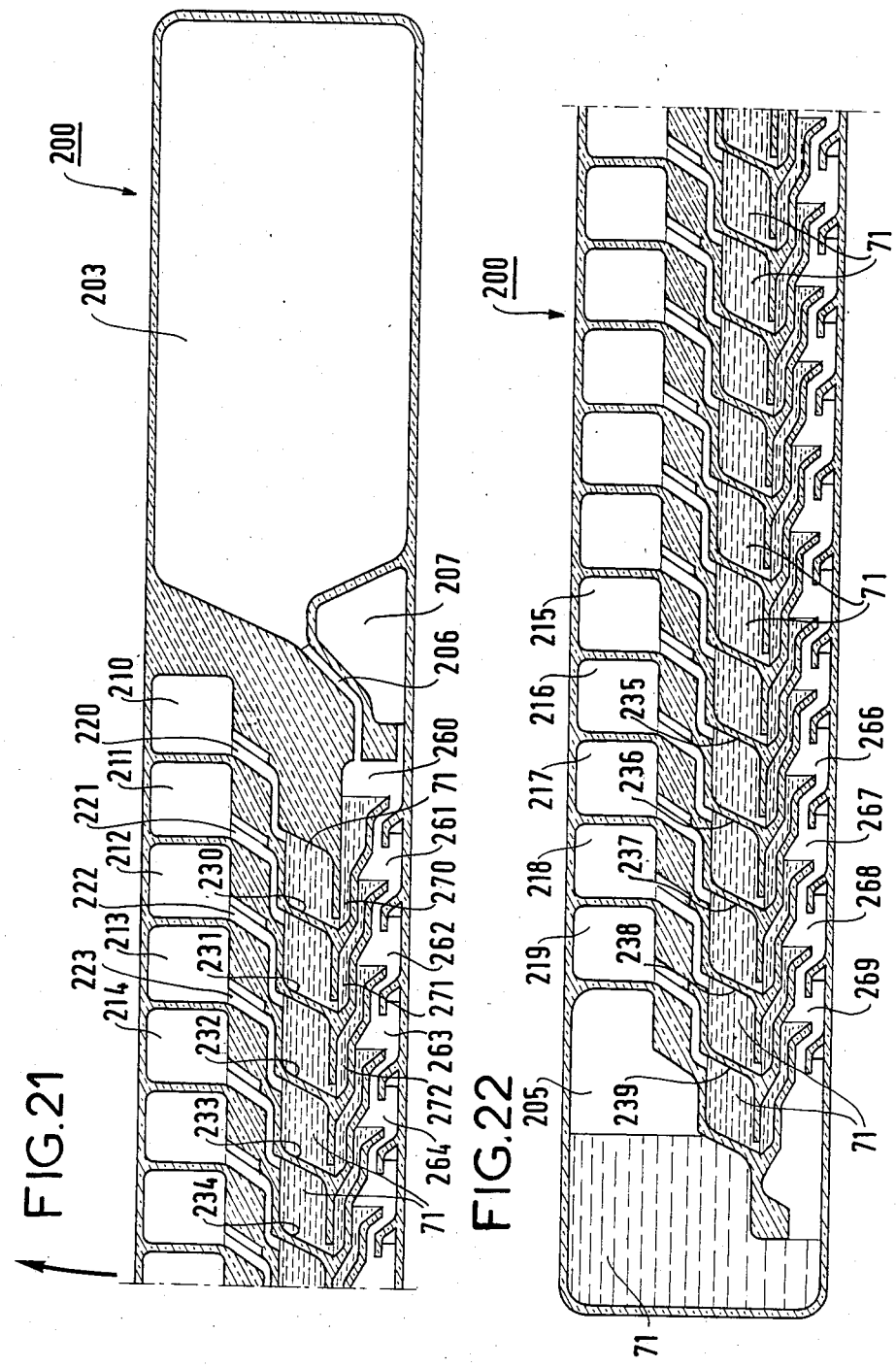

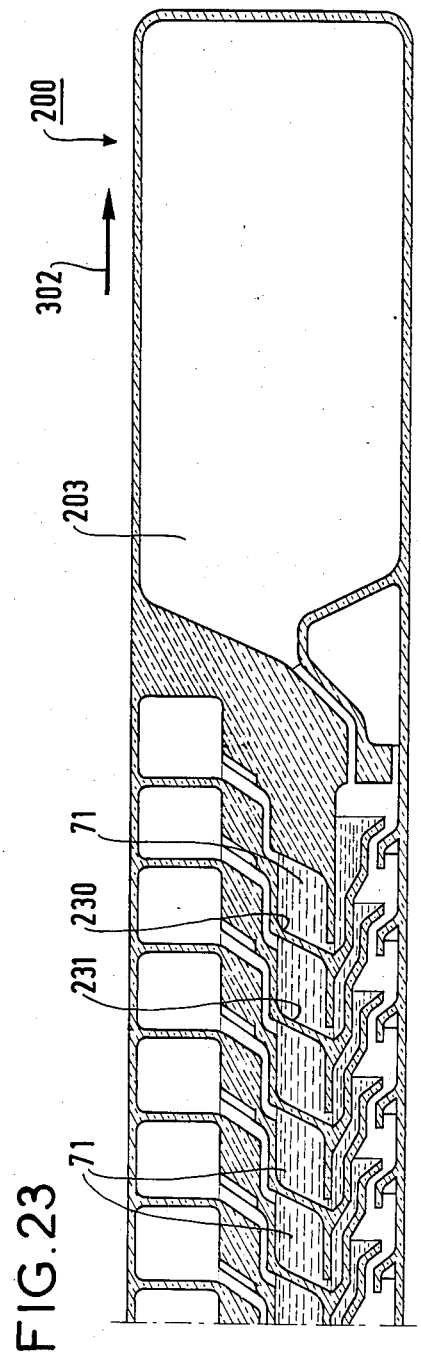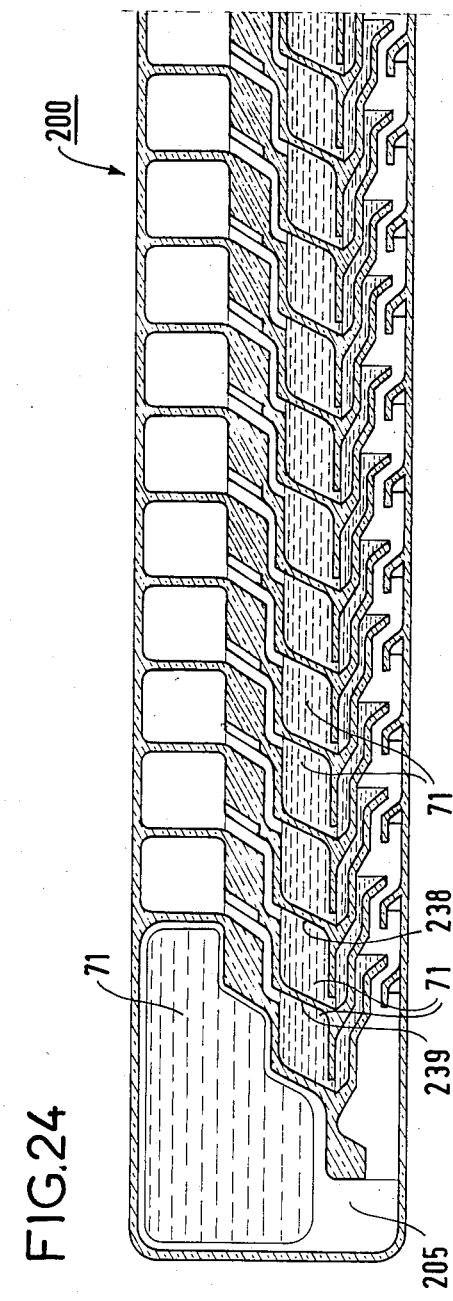

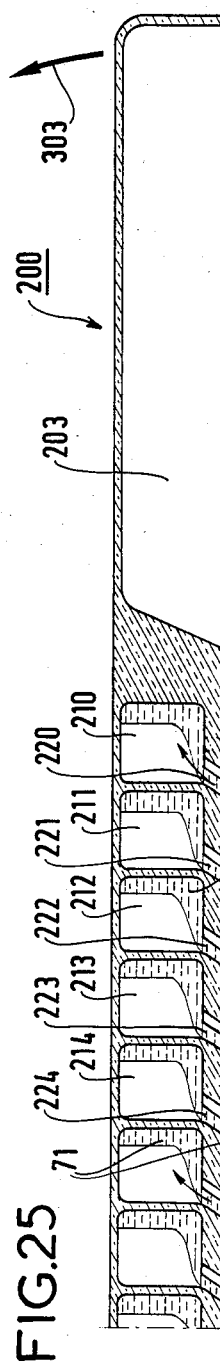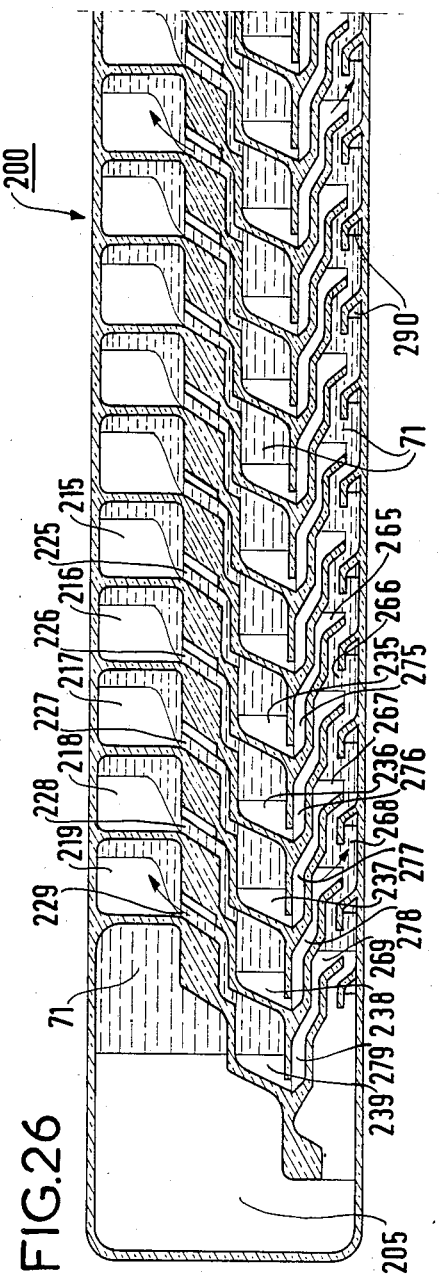

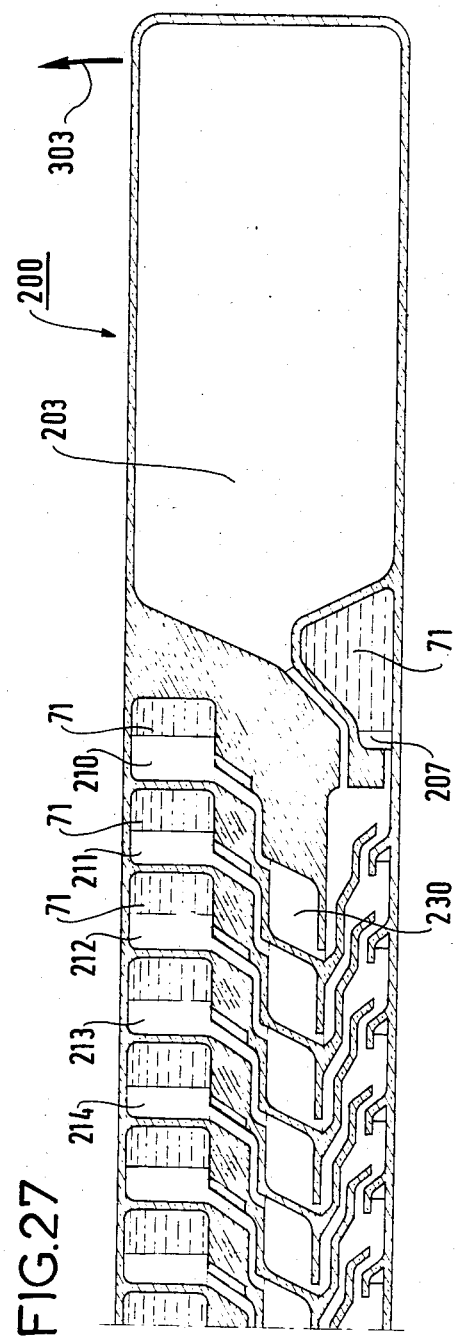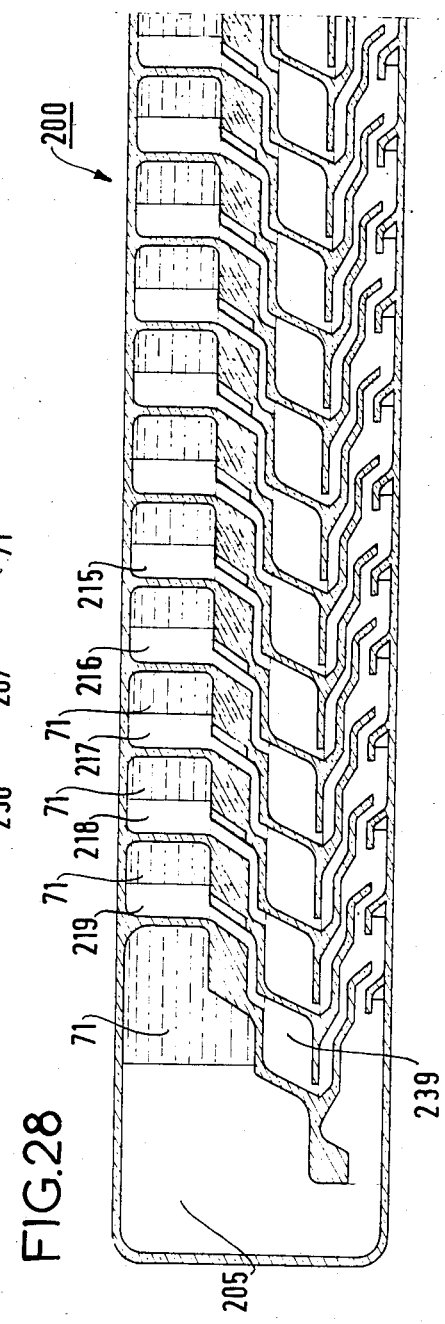

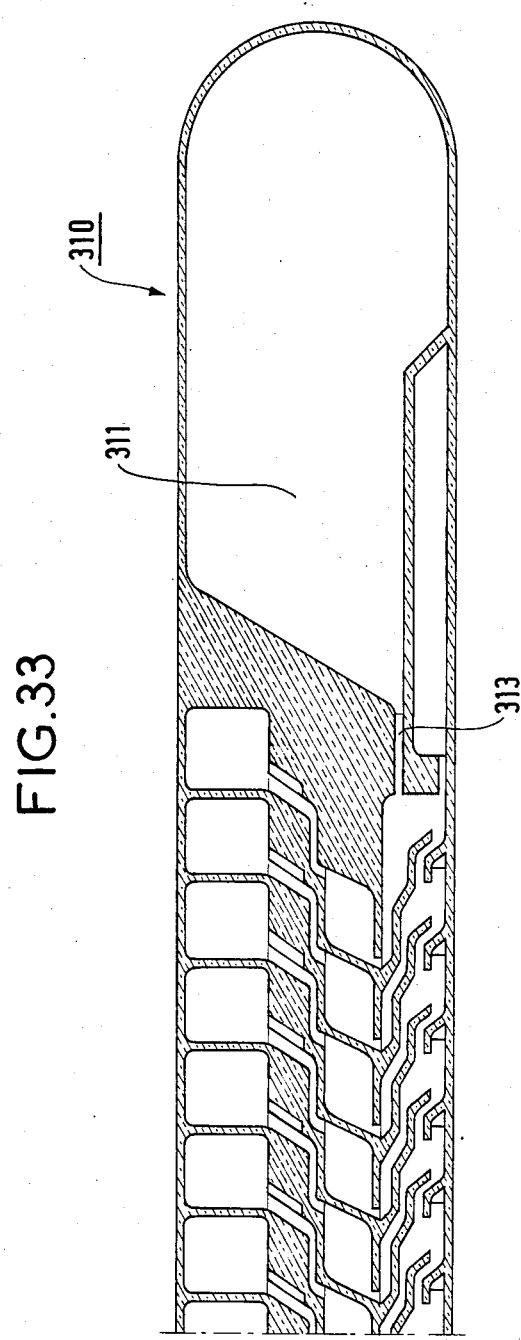

METHOD OF PERFORMING MEDICAL ANALYSES, AND A CONDITIONING STRIP AND APPARATUS FOR PERFORMING THE METHOD

The present invention relates to a method of performing medical analyses, and in particular to performing antibiograms and bacteriologically identifying colonies of micro-organisms. The invention also relates to a conditioning strip and to apparatus for performing the method.

BACKGROUND OF THE INVENTION

In a known method, a sample of a micro-organism colony is taken from an isolation box and seeded in a tube containing a liquid culture medium, the tube is then placed in an oven at 37° C. for a period of at least three or four hours. An operator then looks to see how the colony has developed, and if it has developed sufficiently the operator dilutes the colony to obtain an inoculum of about 10 ml. The inoculum is then placed in a circularly symmetrical analyzer as described in French patent No. 2 280 895. This analyzer has a central receiving well which is closed by a stopper, and a plurality of analysis chambers disposed around the central well. These analysis chambers are connected to the central well via measuring antechambers. The analysis chambers initially contain reagents suitable for performing an antibiogram or an identification biogram. The operator puts the analyzer on a centrifuge in order to insert the inoculum simultaneously and in measured quantities into each of the analysis chambers. The analyzer is then placed in an oven at 37° C. for a period of five to eight hours. Thereafter the analyzer is inserted into a photometer in order to read the results.

Preferred embodiments of the present invention considerably simplify the work to be performed by the operator by making the analysis method capable of being completely automated under conditions of optimum sterility.

SUMMARY OF THE INVENTION

The present invention provides a method of performing medical analyses of the identity biogram and of the antibiogram type, the method making use:

firstly of longitudinal conditioning strips made of transparent plastic material and including a culture enclosure at one end containing a liquid medium, and three series of longitudinally aligned chambers which are parallel to one another, said series comprising a series of reaction chambers containing reagents, a series of volume-measuring antechambers for measuring out volumes which are smaller than the volumes of the reaction chambers, and a series of overflow chambers, with each measuring antechamber being connected via a first capillary duct to a reaction chamber and via a second capillary duct to an overflow chamber;

and secondly a thermostatically controlled enclosure containing:

a central turntable;

a peripheral ring which is coplanar and coaxial with the central turntable, said ring including radial housings for a plurality of conditioning strips, and being suitable for step-by-step rotation; and a gantry extending diametrically over the rotary assembly and supporting optical means such as a turbidimeter and a photometer;

said method comprising the following steps:

directly inoculating a bacterial colony into the liquid medium contained in the culture enclosure of a conditioning strip;

placing the strip in the thermostatic enclosure by inserting it into one of the radial housings of the peripheral ring, with the culture medium being stirred by rotating said peripheral ring;

using the turbidimeter to monitor the transparency of the culture medium liquid each time said liquid passes under the gantry, and when said transparency is satisfactory, the strip is shifted radially along a radius of the turntable to be subjected to a first centrifuging operation which has the effect of filling the measuring antechambers with liquid, the strip is then shifted onto another radius of said turntable and is subjected to a second centrifuging operation which has the effect of emptying the measuring antechambers and of inserting a measured quantity of liquid into each reaction chamber:

the strip is then shifted back into its radial housing in the peripheral ring, and the photometer is used to monitor the reactions in its various reaction chambers each time it passes under the gantry; and when the reactions in the reaction chambers have been completed, the results of the photometric measurements are transmitted to a programmed computer.

The present invention also provides a conditioning strip for performing the above method; the strip comprises a container and a lid made of transparent plastic material, and at a first end it has said culture enclosure which is closed by a stopper and which is suitable for containing a liquid culture medium, said culture enclosure opening out into a first overflow chamber which communicates in turn via a capillary channel with a first measuring antechamber and via a duct with a second overflow chamber, said first measuring antechamber communicating via a first capillary duct with a first reaction chamber suitable for containing a reagent, said second overflow chamber communicating in turn with a second measuring antechamber and with a third overflow chamber, said second measuring antechamber also communicating with a second reaction chamber, and so on up to an n-th overflow chamber, and an n-th measuring antechamber and its associated n-th reaction chamber and an end overflow chamber, the n measuring antechambers being aligned and lying in the middle of the container, the n reaction chambers and the n overflow chambers being respectively aligned along the two longitudinal side walls of said container and being longitudinally offset towards said culture enclosure relative to the n measuring antechambers, the volume of said measuring antechambers being less than the volume of said reaction chambers.

Said container is advantageously made of a single molding of plastic material, and a thin sheet of transparent plastic material is preferably glued or welded to the bottom of said container.

In a variant, said stopper for the culture enclosure is connected to a tape which is locked in position by a drop of wax which has been poured into the orifice for communication between the culture enclosure and the first overflow chamber.

Various reagents which may be pellets or freeze-dried solids are placed in the reaction chambers and a liquid is placed in the culture enclosure. The set of chambers is closed by the container lid, the assembly is sterilized, and wrapped in sterile wrapping prior to use.

The present invention also provides apparatus for automatically performing the method, said apparatus comprising:

an enclosure comprising a supporting table and a transparent lid together with means for regulating the temperature within the enclosure;

said supporting table being provided with:

a central turntable together with means for causing it to rotate about a vertical axis, said turntable having a diametrically extending groove whose width is slightly greater than the width of a conditioning strip;

a peripheral ring which is coplanar and coaxial with said central turntable, said ring including means for causing it to rotate step-by-step independently from said central turntable, and having a plurality of radial housings for receiving conditioning strips; and a gantry disposed over said peripheral ring and supporting firstly mechanical means for shifting a conditioning strip from a radial housing in said ring into the groove of said turntable, and vice versa, and secondly a turbidimeter and a photometer, said turbidimeter being situated in the vicinity of the inside diameter of said ring over the zone of a radial housing which receives the culture enclosure of a strip, and said photometer having n read heads situated over the zone of a housing in the ring which receives the n reaction chambers of a strip;

said apparatus further including a central control unit for the above-mentioned means.

BRIEF DESCRIPTION OF THE DRAWINGS

An implementation of the invention is described with reference to the accompanying drawings, in which:

FIG. 2 is an elevation view in partial section through a conditioning strip used in the method in accordance with the invention;

FIG. 3 is a plan view of the strip shown in FIG. 2;

FIGS. 11 to 14 are diagrammatic cross-sections through the apparatus shown in FIG. 1, and show a FIG. 2 strip in various different positions;

FIGS. 19 and 20 show the initial stages of antechamber filling during a first centrifuging operation on the FIG. 4 strip;

FIGS. 21 and 22 are similar views to FIGS. 19 and 20 after a first centrifuging operation;

FIGS. 23 and 24 show the strip shown in FIGS. 21 and 22 in a rest state after the first centrifuging operation;

FIGS. 25 and 26 show the initial stages of reaction chamber filling in the strip during a second centrifuging operation;

FIGS. 27 and 28 are similar views to FIGS. 25 and 26 showing the end of the second centrifuging operation;

FIG. 33 is a section view on a larger scale through one end of the strip shown in FIGS. 31 and 32.

MORE DETAILED DESCRIPTION

Figure 1:
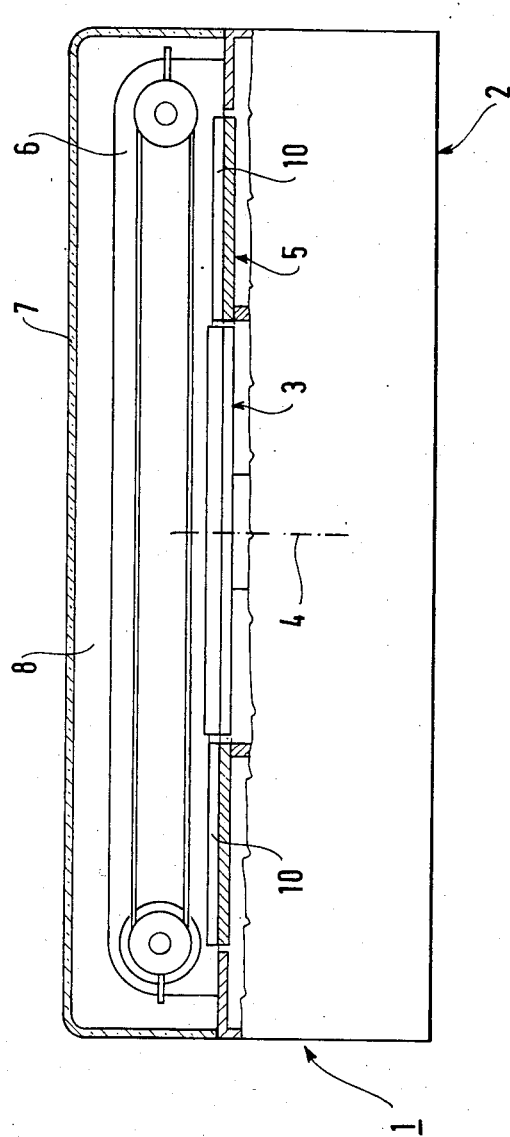
FIG. 1 is a diagrammatic elevation view in partial section through apparatus for performing the method in accordance with the invention.

FIG. 1 is a highly diagrammatic elevation in half-section through apparatus for performing the method in accordance with the invention. The apparatus comprises a cabinet 1 comprising a support table 2 for a turntable 3 which rotates about an axis 4 and for a ring 5 which is substantially coplanar with the turntable and which is capable of rotating about the axis 4. A gantry 6 is fixed above this assembly and supports mechanical means and optical means which are described below.

The top of the support table 2 is covered by a transparent lid 7 which defines an enclosure 8 in which temperature conditions may be predetermined and held fixed, for example at 37° C.

The FIG. 1 apparatus is intended to receive a plurality of conditioning strips 200 of the kind shown in FIGS. 2 and 3.

FIGS. 2 and 3 are an elevation view in partial section and plan view, also in partial section, of a conditioning strip 200 which may be about 13 cm long, about 2 cm wide, and about 1 cm high in a longitudinal portion of reduced height.

The strip is made by assembling a portion 201 which constitutes a container and a portion 202 which constitutes a lid, said portions being advantageously made of molded transparent plastic material. The bottom of the container 201 is fixed to a plate 209 which is also made of transparent plastic material. The strip 200 has a culture enclosure 203 at a first end, and the top of the culture enclosure has an opening 208 which is closed a stopper 204.

Figure 4:
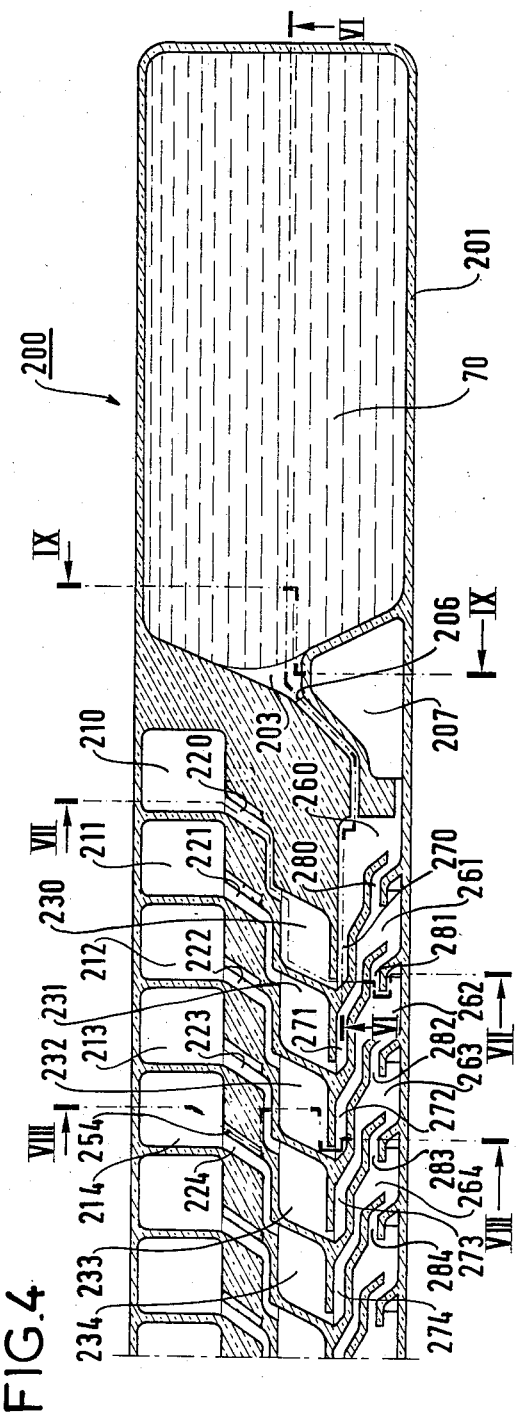
FIG. 4 is a section view on a larger scale through the end of the FIG. 2 strip which includes the culture enclosure.
Figure 5:
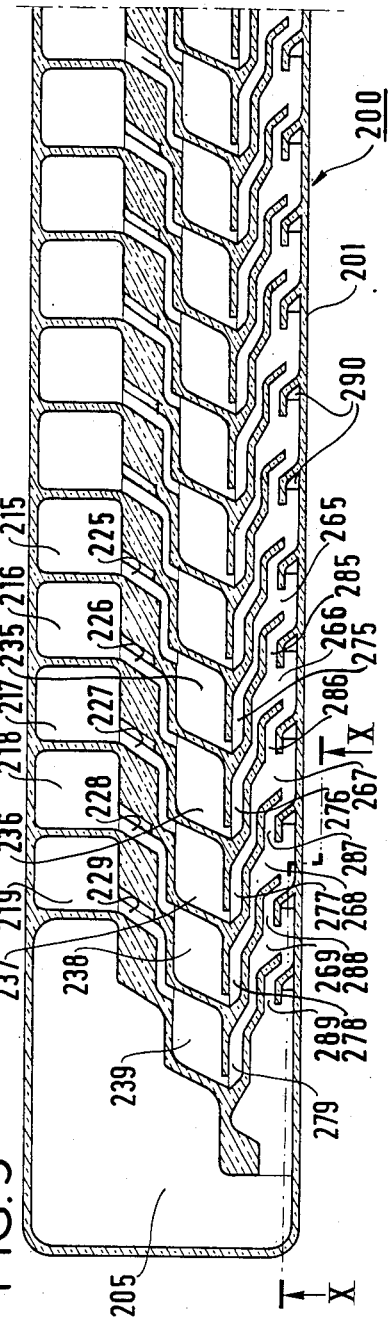
FIG. 5 is a similar view to FIG. 4 showing the other end of the FIG. 2 strip.
Figure 6:
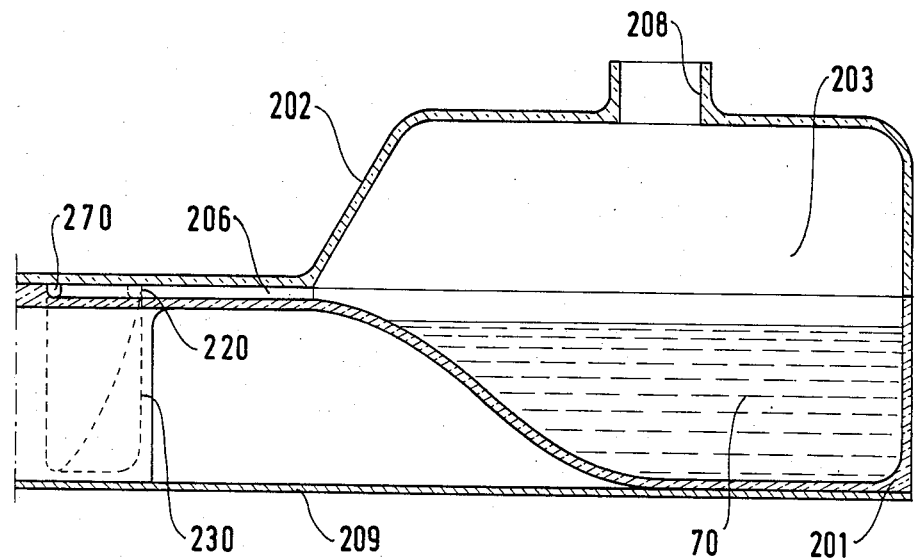
FIG. 6 is a section on a line VI—VI of FIG. 4.

The interior of the container 201 is shown in greater detail in the longitudinal sections of FIGS. 4 and 5, where FIG. 4 shows the end of the strip which includes the culture enclosure, and FIG. 5 shows the other end thereof. FIGS. 6 to 10 are cross-sections showing additional details.

These figures show a culture enclosure 203 for receiving a culture medium 70 and which may have a volume of more than 800 microliters. It communicates with the other chambers in the container via a duct 206.

The strip 200 includes n reaction chambers for receiving reagents which are freeze-dried or in pellet form, together with a measured quantity of the culture medium 70 after it has been seeded. n is advantageously equal to twenty, but in order to simplify the drawings, only ten of these reaction chambers have been given reference numerals: 210 to 219. The reaction chambers are aligned side-by-side along one of the longitudinal walls of the container 201 and they are generally cubical in shape.

Figure 8:
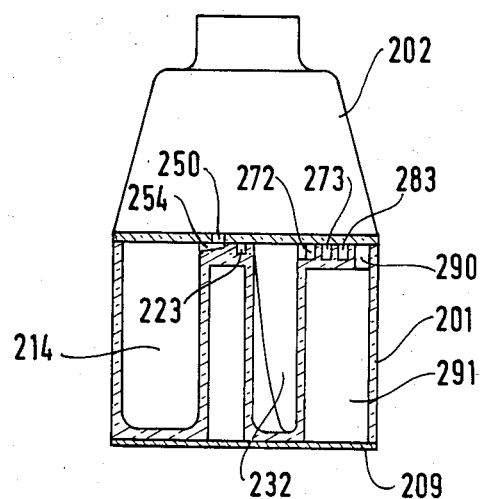
FIG. 8 is a section on a line VIII—VIII of FIG. 4.
Figure 9:
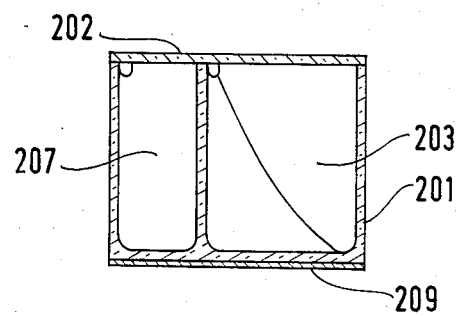
FIG. 9 is a section on a line IX—IX of FIG. 4.

As can be seen more clearly in FIGS. 3 and 8, each reaction chamber communicates individually with the outside environment via a respective duct passing through the top face of the container 201 and situated opposite to an orifice 250 provided through the lid 202. For example, the chamber 214 has a duct 254. The duct 254 and the corresponding orifice 250 are slightly offset relative to the reaction chamber per se, so as to allow air to pass freely into the reaction chamber, but to retain particles which may fall in from the outside.

The reaction chambers 210 to 219 are connected via respective capillary ducts 220 to 229 to n antechambers 230 to 239 of calibrated volume. The antechambers are aligned in parallel with the reaction chambers 210 to 219, but are longitudinally offset relative thereto towards the end chamber 205. The ducts 220 to 229 are L-shaped. The calibrated volume of each antechamber (e.g. 40 microliters) is considerably less than the volume of a reaction chamber, e.g. about one-half thereof.

The conditioning strip 200 further comprises a plurality of overflow chambers. Firstly there is the end overflow chamber 205, then there are n individual overflow chambers referenced 260 to 269 which are connected to respective ones of the antechambers 230 to 239 via respective channels 270 to 279. The overflow chambers 260 to 269 are aligned side-by-side along the other longitudinal side wall of the container 201 and are longitudinally offset towards the culture enclosure 203 relative to the corresponding antechambers. The channels 270 to 279 are L-shaped and are oriented relative to the ducts 220 to 229 in a manner which is substantially symmetrical about a plane running orthogonally to the plane of FIGS. 4 and 5.

Figure 7:
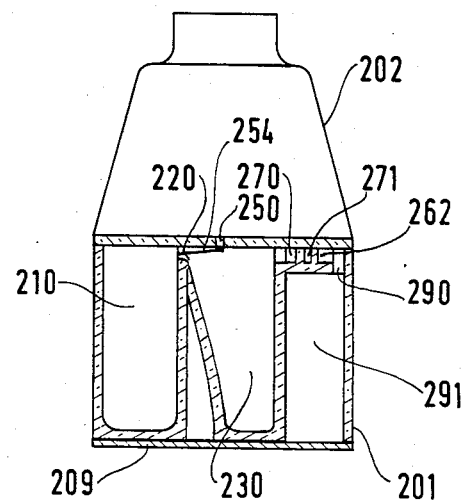
FIG. 7 is a section on a line VII—VII of FIG. 4.
Figure 10:
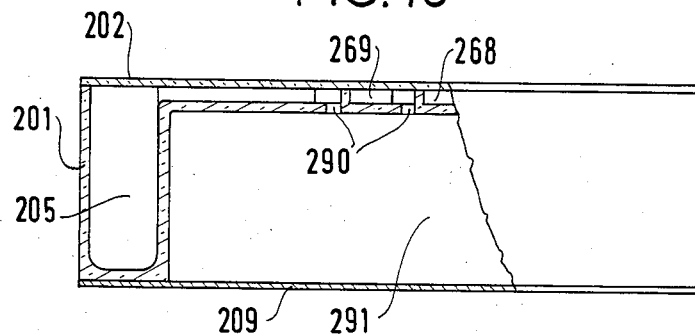
FIG. 10 is a section on a line X—X of FIG. 5.

In addition, the n overflow chambers communicate with one another via ducts 280 to 288 which are substantially parallel to the channels 270 to 279, and with a common longitudinal gutter 291 via orifices 290 (see FIGS. 7, 8, and 10). The channel 289 puts the overflow chamber 269 into communication with the end overflow chamber 205. Finally, the overflow chamber 260 at the other end of the strip communicates with the overflow chamber 207 adjacent to the culture enclosure 203.

Once suitable reagents have been disposed in the n reaction chambers, and a suitable culture medium 70 has been disposed in the culture enclosure 203, the lid 202 is welded to the container 201.

The strip filled in this way is sterilized and is stored in sterile wrapping.

For reasons which are explained below, a strip 200 is moved in various ways over the turntable 3 or over the ring 5 of the cabinet shown in FIG. 1. There are four main positions of the strip 200 and these appear in FIGS. 11 to 14 where the apparatus is shown in diagrammatic section and in corresponding FIGS. 15 to 18 where the apparatus is shown in a partial plan view.

The ring 5 has a plurality of radial housings 10 for receiving strips 200. For example, its outside diameter may be about 40 centimeters and it may have sixty housings. Drive means diagrammatically represented by two gear wheels 32 and 34 serve to rotate the ring 5 around its axis of symmetry 4, and these drive means are used to provide a step-by-step drive causing the ring to advance in jerks, e.g. by 1 jerk per second.

The central turntable 3 has a diameter of about 26 centimeters and may be caused to rotate rapidly about its axis 4 by drive means represented by gear wheels 31 and 33. The turntable includes a diametrically extending groove 30 suitable for receiving a strip 200, together with pegs 45 and 48 suitable for holding the strip in a first half or a second half of the groove 30.

A strip 200 is moved from a housing 10 in the ring 5 into the groove 30 on the turntable 3 by means of a mechanical chain system 40 driven by shafts 41 and 42 and provided with drive fingers 44 and 43. This mechanical strip-driving system is fixed to the gantry 6 on the cabinet 1.

Figure 15:
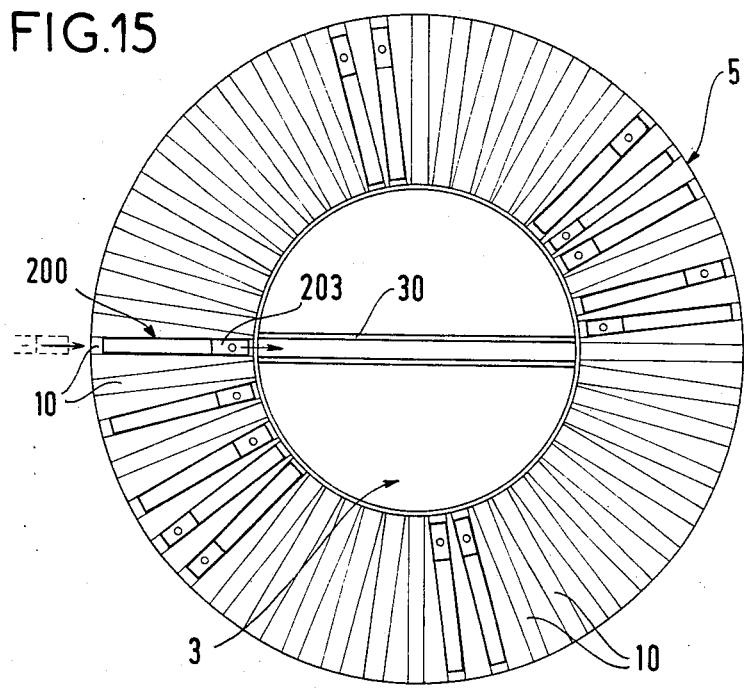
FIGS. 15 to 18 are plan views of the FIG. 1 apparatus and correspond to FIGS. 11 to 14 respectively.

The initial position of the strip 200 is shown in FIGS. 11 and 15. The strip is then pushed by the finger 44 onto one radius of the groove 30 in the turntable 3 and it is held thereon by the peg 45 (see FIGS. 12 and 16). The shafts 41 and 42 are then reversed to take the finger 44 away from the strip 200.

Figure 17:
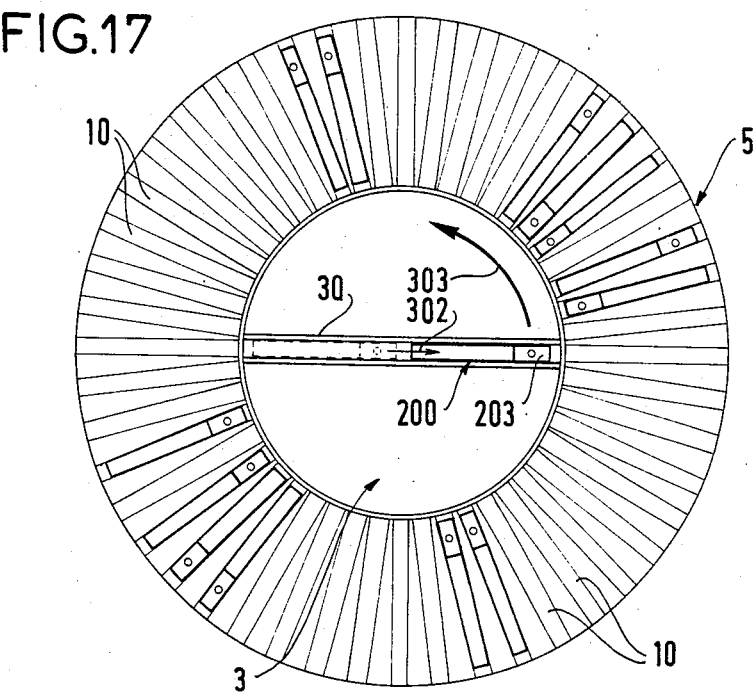

FIGS. 13 and 17 show the strip 200 disposed in the other half of the groove 30, with the peg 45 being removed and with the peg 48 now serving to hold the strip.

Figure 18:
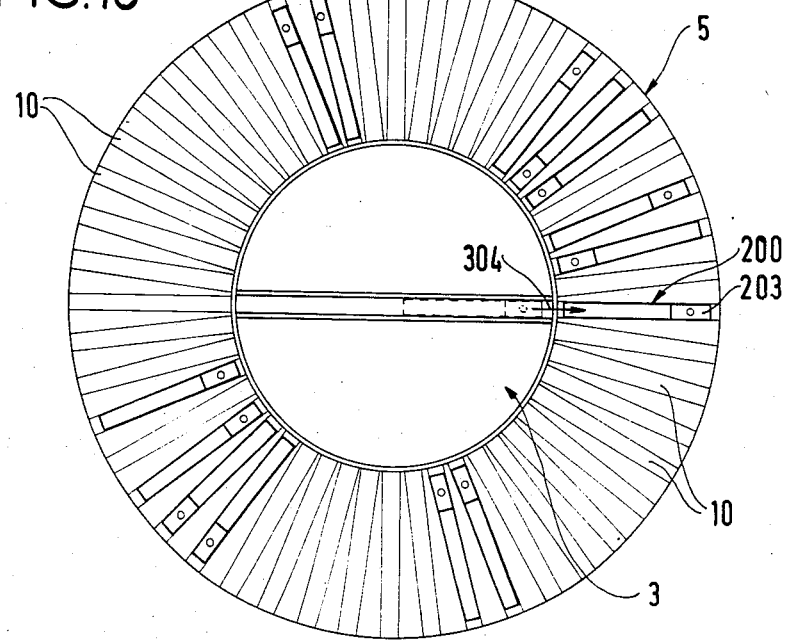

Finally, FIGS. 14 and 18 show the strip 200 returned to its housing 10, again by means of the drive finger 44.

The gantry 6 on the cabinet 1 also supports two types of optical device:

a turbidimeter 75 situated near the inside diameter of the ring 5 in such a position as to be located above the culture enclosure 203 of the strip 200 when the strip is in its normal position in its housing 10, prior to being moved onto the turntable 3; and a photometer 80 having n read heads 81, using optical fibers for example, likewise situated over the ring 5 in such a manner as to locate the read heads above the n reaction chambers when the strip 200 is in its normal position in its housing 10 after being placed on the turntable 3.

The various mechanical, temperature control, optical, and electronic devices are operated under the control of a central control unit, not shown.

The method in accordance with the invention is described in detail below. A sterile strip 200 as shown in FIGS. 2 to 10 is taken and the stopper 204 removed to enable the culture medium 70 in the culture enclosure 203 to be directly inoculated with a colony of microorganisms taken from a culture on gelose. Unlike prior methods, there is no point in preparing an inoculum having a fixed density of germs. A liquid sample 71 for analysis is thus obtained. After replacing the stopper 204, the operator inserts the strip 200 into the cabinet in accordance with the invention and has nothing further to do with it until entering up the results of the various analyses performed.

The strip 200 is thus placed in a housing 10 of the ring 5 (see FIG. 15) in such a manner that the culture enclosure 203 is located close to the inside diameter of the ring. Naturally, a plurality of strips 200, up to a maximum of 60, may be inserted successively or simultaneously into the housings 10.

The ring 5 is rotated stepwise at one jerk per second and thus stirs the liquid 71 and also causes each culture enclosure 203 to pass under the turbidimeter 75 once per minute (see FIG. 11). The transparency of the culture medium is read automatically through the plastic material of the strip 200. So long as the germ concentration in the liquid 71 is too small, the relevant strip remains in the ring 5. Once the desired concentration has been reached, the central control unit stops rotation of the ring and controls the chain 40 to move the strip 200 into the groove 30 on the central turntable 3 (see FIGS. 12 and 16), with the culture enclosure 203 then being located near to the axis of rotation 4.

Figure 16:
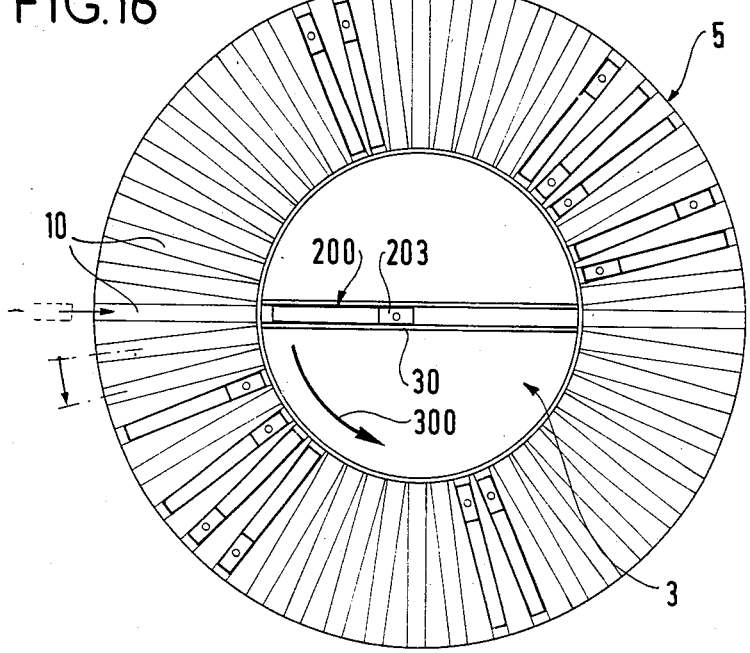

While the ring 5 continues its stepwise rotation, the strip 200 is held in the groove 30 and is subjected to a first centrifuging operation which is represented by the arrow 300 in FIG. 16.

FIGS. 19 and 20 show the liquid 71 progressing along the strip, while FIGS. 21 and 22 show how the liquid 71 is distributed at the end of the centrifuging operation.

In FIG. 19, it can be seen that the liquid 71 moves in the direction of arrow 301 towards the duct 206, the first overflow chamber 260, the channel 270, and the first antechamber 230. The orientation of channel 220 is such that the liquid cannot enter therein. As a result, the overflow chambers and the antechambers 230 to 234 are filled successively. FIG. 20 shows the antechambers 235 to 234 still empty. At a later stage (FIGS. 21 and 22) the culture enclosure 203 is completely empty, all the antechambers are full, and excess liquid 71 is located in the intermediate overflow chambers and in the end overflow chamber 205. The rest position of the strip 200 after the centrifuging operation marked by arrow 300 appears in FIGS. 23 and 24.

The central control unit then causes the strip to be moved in the direction of arrow 302 (see FIGS. 17 and 13) so that it is located in the second half of the groove 30 with its culture enclosure 203 situated near the periphery of the turntable 3.

A second centrifuging operation is then performed as indicated by arrow 303 in FIGS. 17, 25 and 27.

Figure 29:
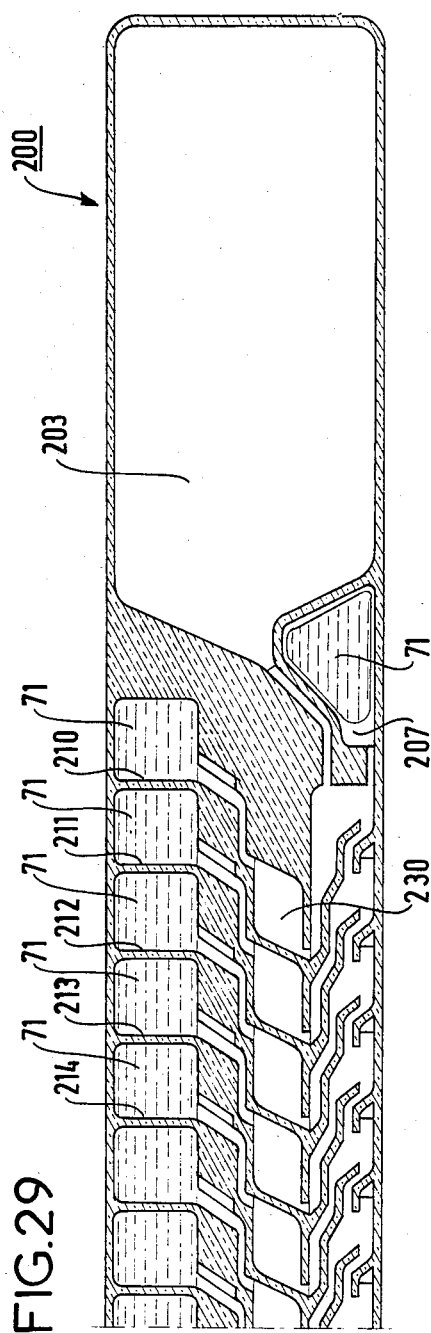
FIGS. 29 and 30 show the strip as shown in FIGS. 27 and 28 but in a rest state after the second centrifuging operation.
Figure 30:
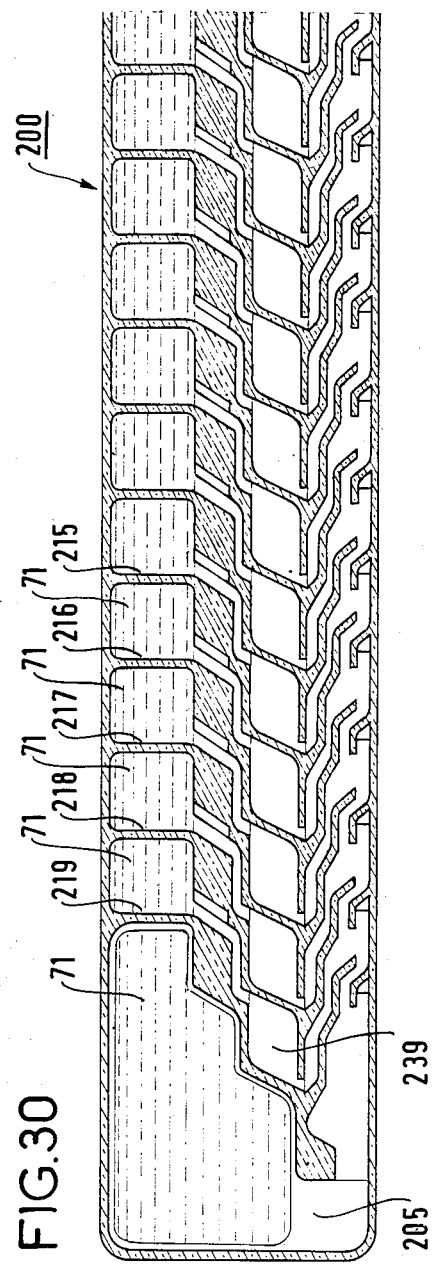

FIGS. 25 and 26 show an intermediate phase during the second centrifuging operation, FIGS. 27 and 28 show the end of the second centrifuging operation, and FIGS. 29 and 30 show the following rest position. Briefly stated, this second centrifuging operation serves to cause a calibrated volume of liquid 71 to move from each antechamber into the corresponding reaction chamber.

As can be seen in FIG. 26, the channels 270 to 279 are oriented relative to the centrifuging direction in such a manner that the liquid 71 flows successively into the overflow chambers 269 to 260 and then 207, and simultaneously via the orifices 290 into the common gutter 291.

However, the ducts 220 to 229 between the antechambers 230 to 239 and the reaction chambers 210 to 219 are oriented in such a manner as to ensure that the reaction chambers are filled (see FIGS. 27 and 28).

At the end of the second centrifuging operation, samples of the liquid 71 are to be found only in the reaction chambers 210 to 219 and in the overflow chambers 207 and 205.

After the centrifuging operation, reactions begin to take place in the reaction chambers 210 to 219 (see FIGS. 29 and 30). When the housing 10 which was initially associated with the strip 20 is aligned with the groove 30, the central control unit causes the strip to be moved back into its housing (see arrow 304 in FIG. 18, and FIG. 14).

The strip 200 continues to rotate with the ring 5 for whatever length of time is required for the reactions. These reactions take place in the enclosure 8 under the best possible conditions at 37° C. A sufficient volume of air remains above the sample of liquid 71 in each reaction chamber, and in any case the volume of air each reaction chamber is in communication with the outside air.

On each revolution, whenever the strip 200 passes underneath the photometer 80 (see FIG. 14) the photometer performs n measurements on each of the n reaction chambers simultaneously and transmits the results thereof to the control unit which interprets said results and causes them to be printed out on a printer when the reactions have terminated.

Figure 31:
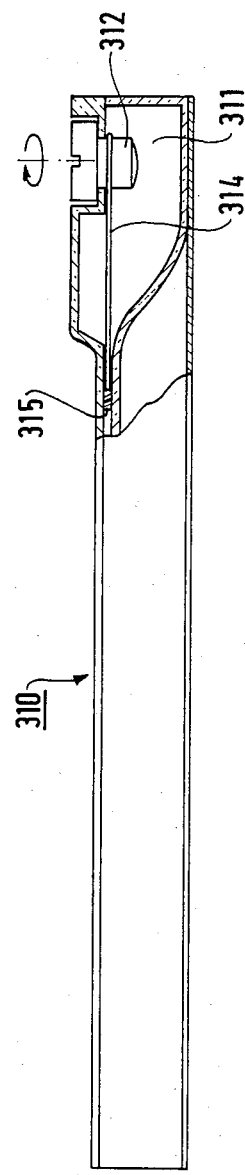
FIG. 31 is an elevation view in partial section through a variant conditioning strip for use in the method in accordance with the invention.
Figure 32:
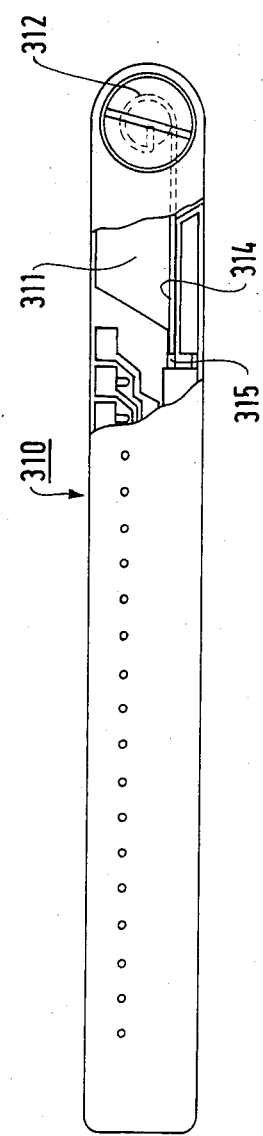
FIG. 32 is a plan view of the strip shown in FIG. 31.

Naturally, the invention is not limited to the embodiments described above. By way of example, various details of the conditioning strip may be modified. Thus, FIGS. 31 to 33 show a strip 310 whose culture enclosure 311 is closed by a stopper 312. The stopper is surrounded by a tape of plastic material 314 having one end which may be inserted into a passage 313 and locked therein by a drop of wax 315 (see FIGS. 31 and 33). In order to inoculate a germ therein, the stopper 312 is rotated and removed, thereby withdrawing the tape and the drop of wax from the passage 313.

Also, the above description relates to vertical reading photometers, but a technically equivalent arrangement could be provided in which the photometers read laterally.

Regardless of the implementation details, the method in accordance with the invention may be fully automated in apparatus which may be called a "microanalyzer" and which has the following important advantages:

Germs may be inserted directly from cultures on gelose and there is no need to adjust the density of the germs in the culture medium before testing. The liquid culture medium is monitored automatically.

A strip may be inserted into the apparatus at any moment, since it is only necessary to stop the outer ring for a few seconds and this has no adverse effect on the reactions which are taking place in other strips. It is no longer necessary to run analyses in batches per sample series. For example, an identity biogram and an antibiogram may be performed simultaneously for thirty patients.

Since handling operations are reduced to a minimum, sterile conditions are optimal.

I claim:

1. A conditioning strip for facilitating medical analyses of the identify biogram and of the antibiogram type and for placement in a thermostatically controlled enclosure containing:

a central turntable;

a peripheral ring which is coplanar and coaxial with the central turntable, said ring including radial housings for a plurality of such conditioning strips, and being mounted for step-by-step rotation; and a gantry extending diametrically over the rotary assembly and supporting optical means such as a turbidimeter and a photometer;

said strip comprising a container and a lid made of transparent plastic material, said strip having a first end fitted with a culture enclosure closed by a stopper and suitable for containing a liquid culture medium, said culture enclosure opening out into a first overflow chamber and communicating in turn via a capillary channel with a first measuring antechamber and a duct with a second overflow chamber, said first measuring antechamber communicating via a first capillary duct with a first reaction chamber suitable for containing a reagent, said second overflow chamber communicating in turn with a second measuring antechamber and with a third overflow chamber, said second measuring antechamber also communicating with a second reaction chamber, and so on up to an n-th overflow chamber, and an n-th measuring antechamber and its associated n-th reaction chamber and an end overflow chamber, the n measuring antechambers being aligned and lying in the middle of the container, the n reaction chambers and the n overflow chambers being respectively aligned along the two longitudinal side walls of said container and being longitudinally offset towards said culture enclosure relative to the n measuring antechambers, the volume of said measuring antechambers being less than the volume of said reaction chambers.

2. A conditioning strip according to claim 1, wherein said container is a single molded piece of plastic material.

3. A conditioning strip according to claim 2, wherein a thin plate of transparent plastic material is fixed to the bottom of said container.

4. A conditioning strip according to claim 1, wherein said stopper for the culture enclosure is connected to a tape which is held by a drop of wax in the orifice which provides communication between the culture enclosure and the first overflow chamber.

5. A conditioning strip according to claim 1 or claim 4 wherein said reaction chambers contain respective reagents in the form of pellets or freeze-dried reagents.

6. A conditioning strip according to claim 1 or claim 4, wherein the strip is sterilized and then wrapped in sterile wrapping.

* * * * *